United States Patent [19]

Romano

[11] Patent Number: 5,509,918
[45] Date of Patent: Apr. 23, 1996

[54] METHOD AND APPARATUS FOR DRILLING A CURVED BORE IN AN OBJECT

[75] Inventor: Jack W. Romano, Seattle, Wash.

[73] Assignee: David Romano, Seattle, Wash.

[21] Appl. No.: 59,834

[22] Filed: May 11, 1993

[51] Int. Cl.⁶ .................................................. A61B 17/56
[52] U.S. Cl. .............................. 606/80; 606/96; 606/180; 408/241 R
[58] Field of Search .................... 606/80, 79, 81, 606/86, 87, 96, 97, 103, 180, 167; 408/1 R, 1 BD, 127, 136, 146, 147, 148, 149, 157, 159, 187, 188, 241 G, 115 R, 115 G, 172 R, 241 R; 81/177.6; 175/61.75, 73, 74, 75

[56] References Cited

U.S. PATENT DOCUMENTS

| | | |
|---|---|---|
| 1,223,938 | 4/1917 | Close . |
| 1,698,952 | 1/1929 | Hoover . |
| 1,822,330 | 9/1931 | Ainslie . |
| 2,291,413 | 7/1942 | Siebrandt . |
| 2,666,430 | 1/1954 | Gispert . |
| 2,747,384 | 5/1956 | Beam . |
| 2,905,178 | 9/1959 | Hilzinger III . |
| 3,554,192 | 1/1971 | Isberner . |
| 3,628,522 | 12/1971 | Kato . |
| 3,697,188 | 10/1972 | Pope . |
| 3,815,605 | 6/1974 | Schmidt et al. . |
| 4,257,411 | 3/1981 | Cho . |
| 4,265,231 | 5/1981 | Scheller, Jr. et al. . |
| 4,312,337 | 1/1982 | Donohue . |
| 4,345,601 | 8/1982 | Fukuda . |
| 4,421,112 | 12/1983 | Mains et al. . |
| 4,541,423 | 9/1985 | Barber . |
| 4,590,929 | 5/1986 | Klein . |
| 4,622,960 | 11/1986 | Tam . |
| 4,941,466 | 7/1990 | Romano ................................ 606/80 |
| 5,002,546 | 3/1991 | Romano ................................ 606/80 |
| 5,017,057 | 5/1991 | Kryger ................................. 408/68 |
| 5,354,300 | 10/1994 | Goble et al. ......................... 606/80 |

*Primary Examiner*—Guy Tucker
*Attorney, Agent, or Firm*—Christensen, O'Connor, Johnson & Kindness

[57] ABSTRACT

A method and apparatus for drilling a curved bore are disclosed, wherein the apparatus includes a handle (20) and a removable cartridge (174) in which cutting bits (240) are disposed to produce the bore. The handle includes a trigger (66), (66'), or (66"), which the user squeezes toward a grip (24) of the handle to both energize a pneumatic motor (42) and to advance the opposed cutting bits in curved arcs at different rates. As the trigger is squeezed, a curved guide arm (234) conveying one of the cutting bits is advanced more rapidly than the other curved guide arm, passing a median point in the bore and then being withdrawn as the other curved guide arm and cutting bit are advanced past the median point. Thus, interference between the two cutting bits is avoided and a clean bore hole is produced. In addition, the removable cartridge minimizes breakage of a flexible drive cable (238) used to transmit rotational force to the cutting bits from rotating left and right extended drive shafts (190 and 192). A straight segment (236) of each curved guide arm is provided adjacent the point where the cutting bit connects to the flexible drive cable, to substantially eliminate stress on the flexible drive cable at that point. Instead, the stress is shifted to a portion of the flexible shaft where its flexibility is greater. A push-button release (122) is provided on a barrel (26') of the handle to facilitate release of retainer pins (106') that engage push bars in the removable cartridge so that the removable cartridge can more easily be disengaged from the barrel.

29 Claims, 11 Drawing Sheets

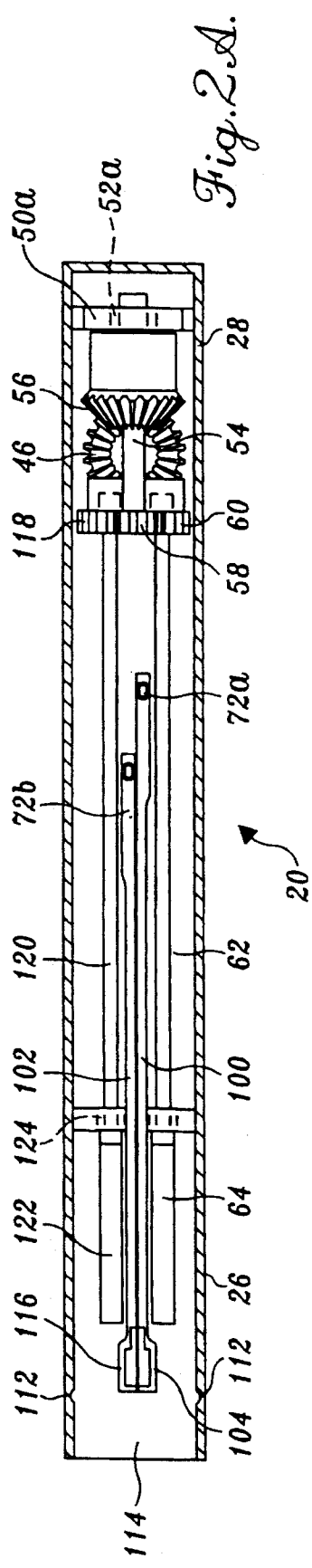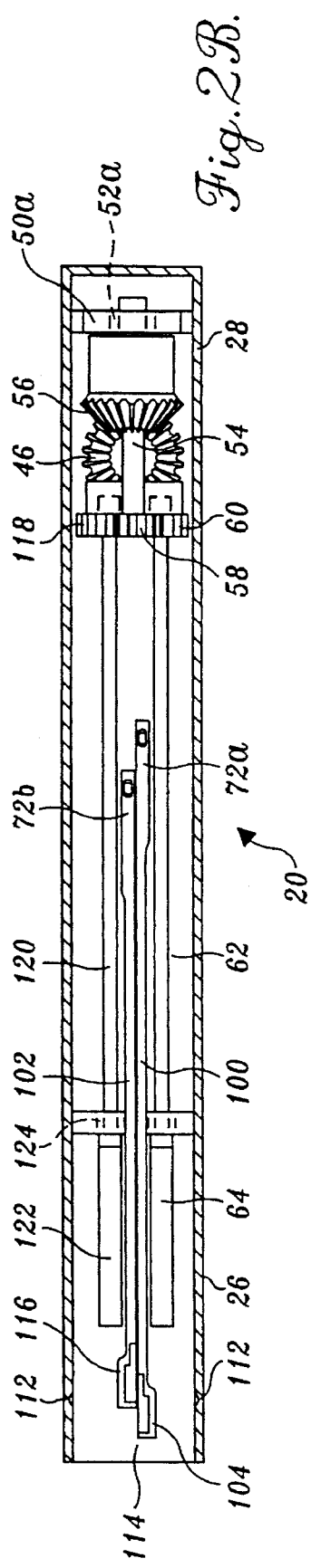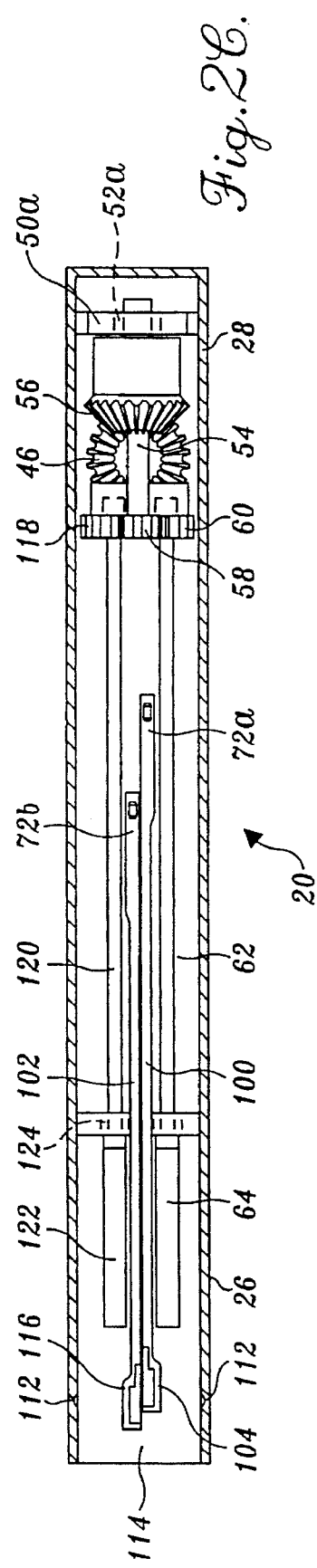

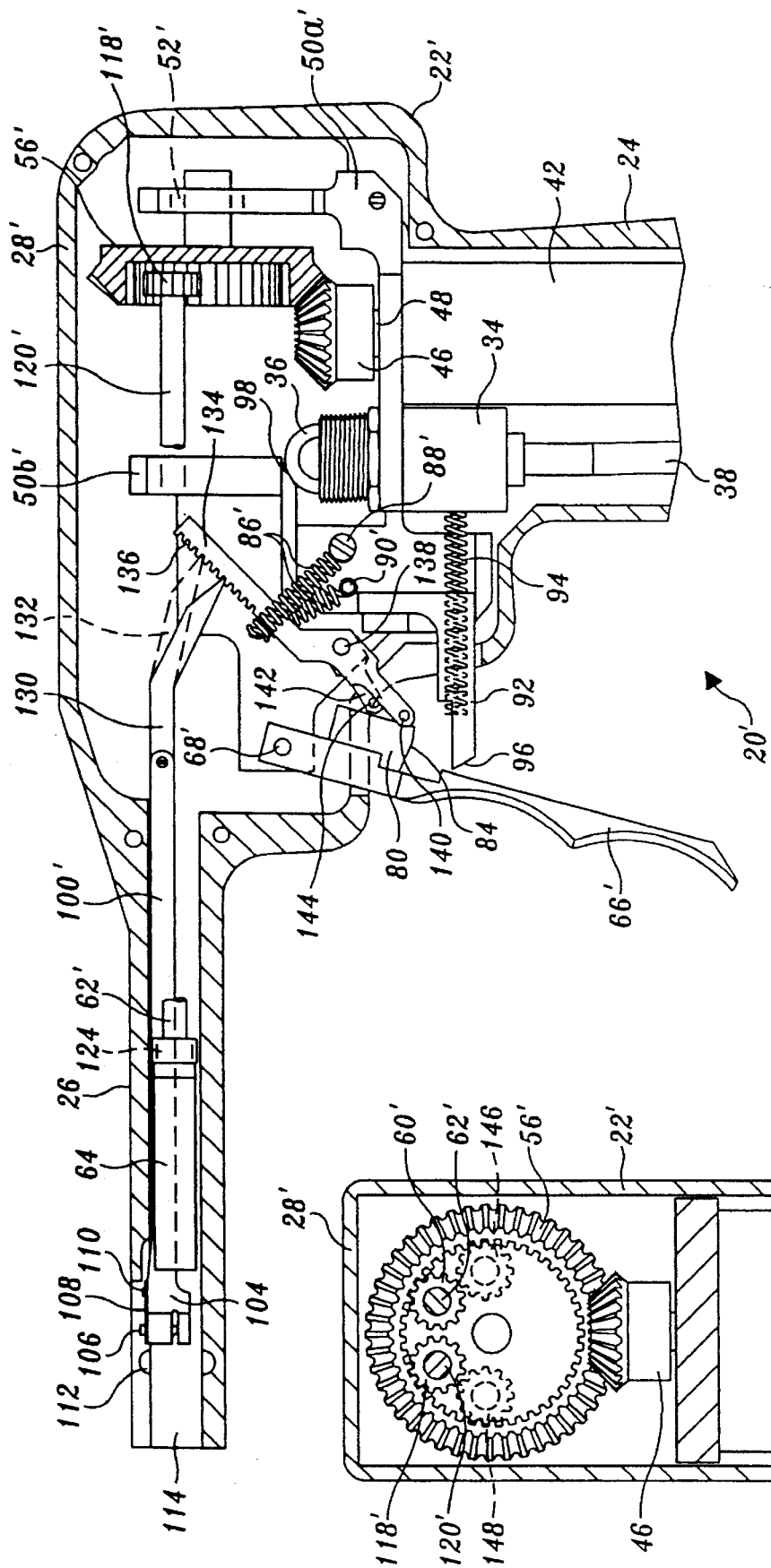

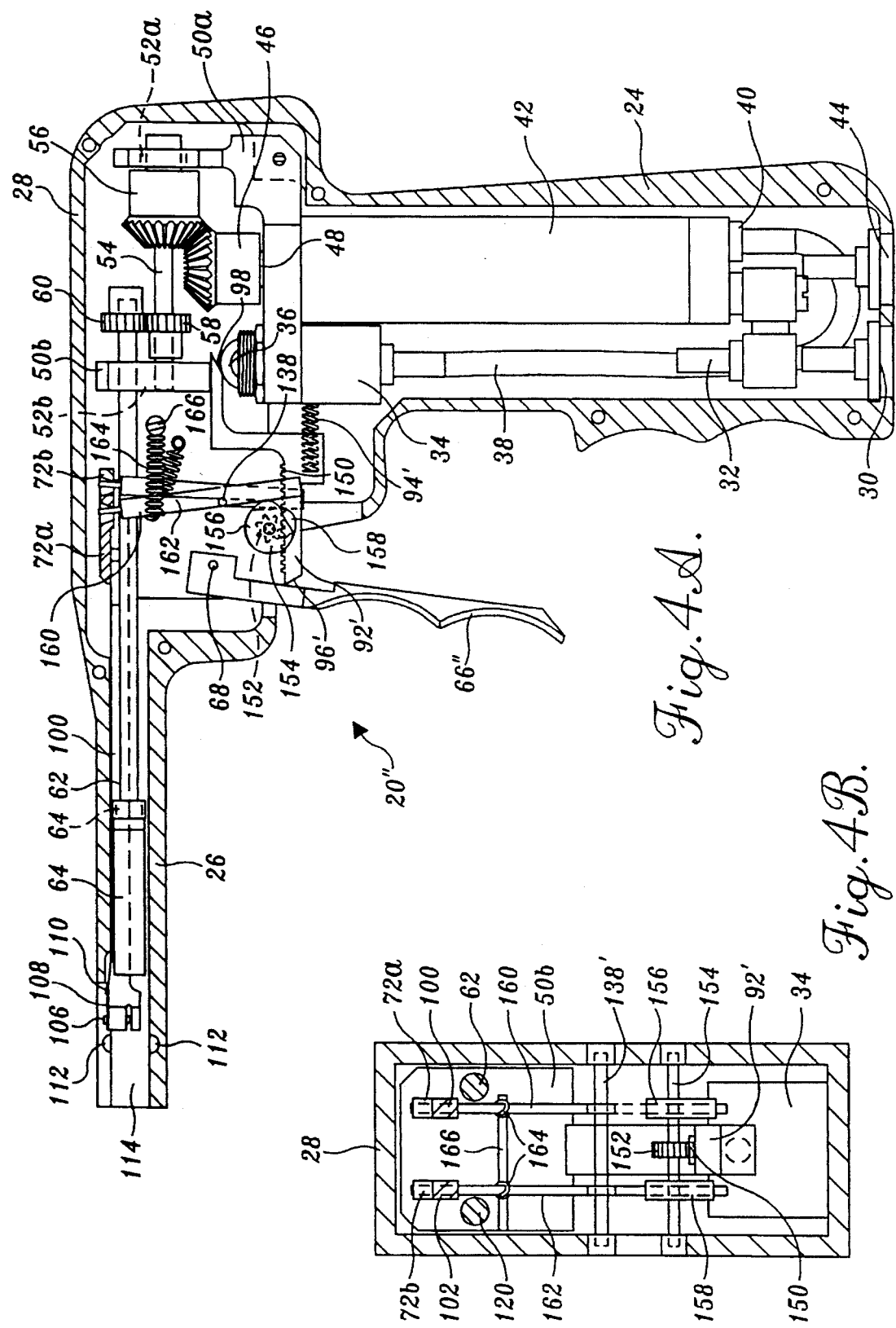

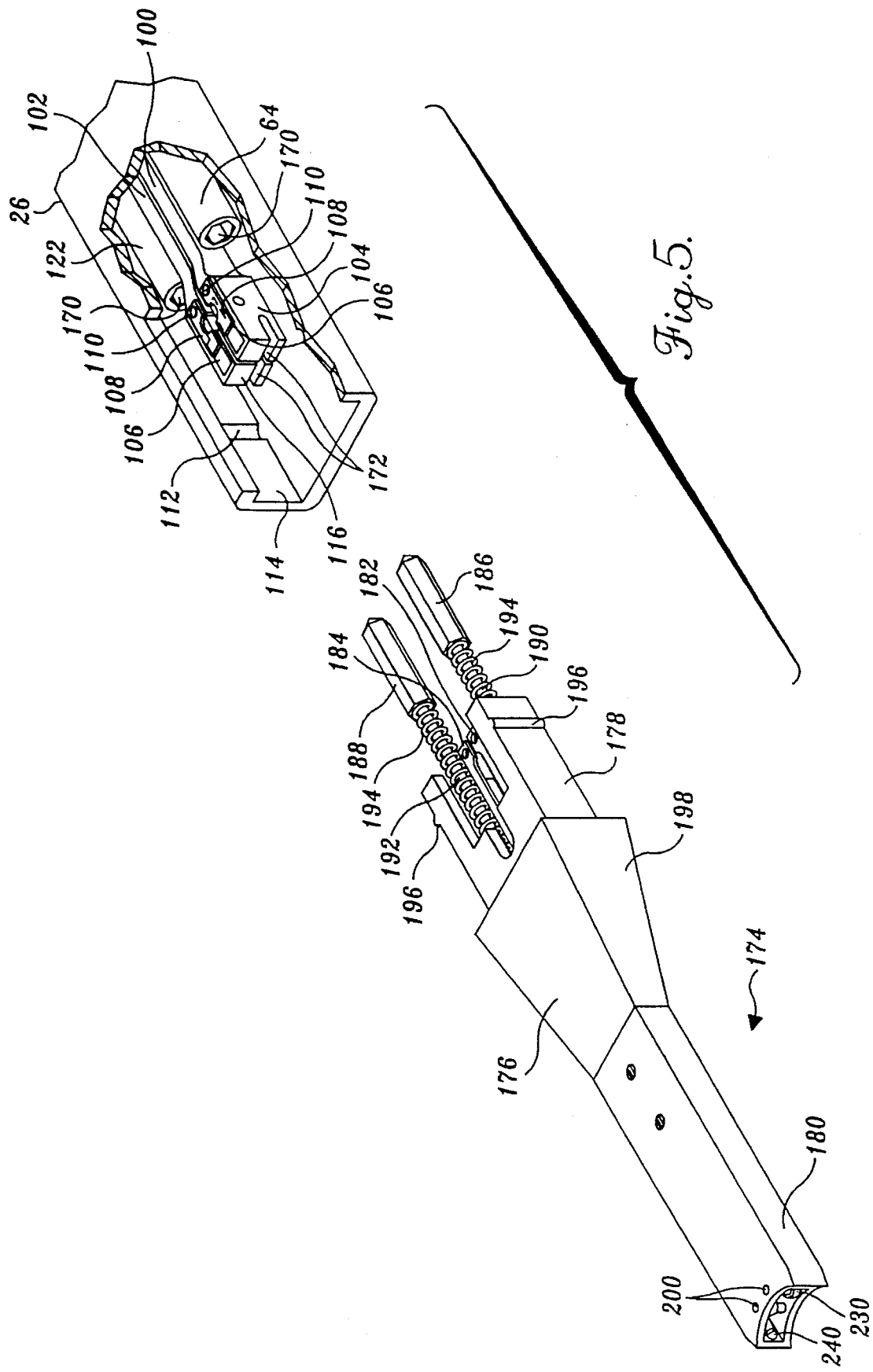

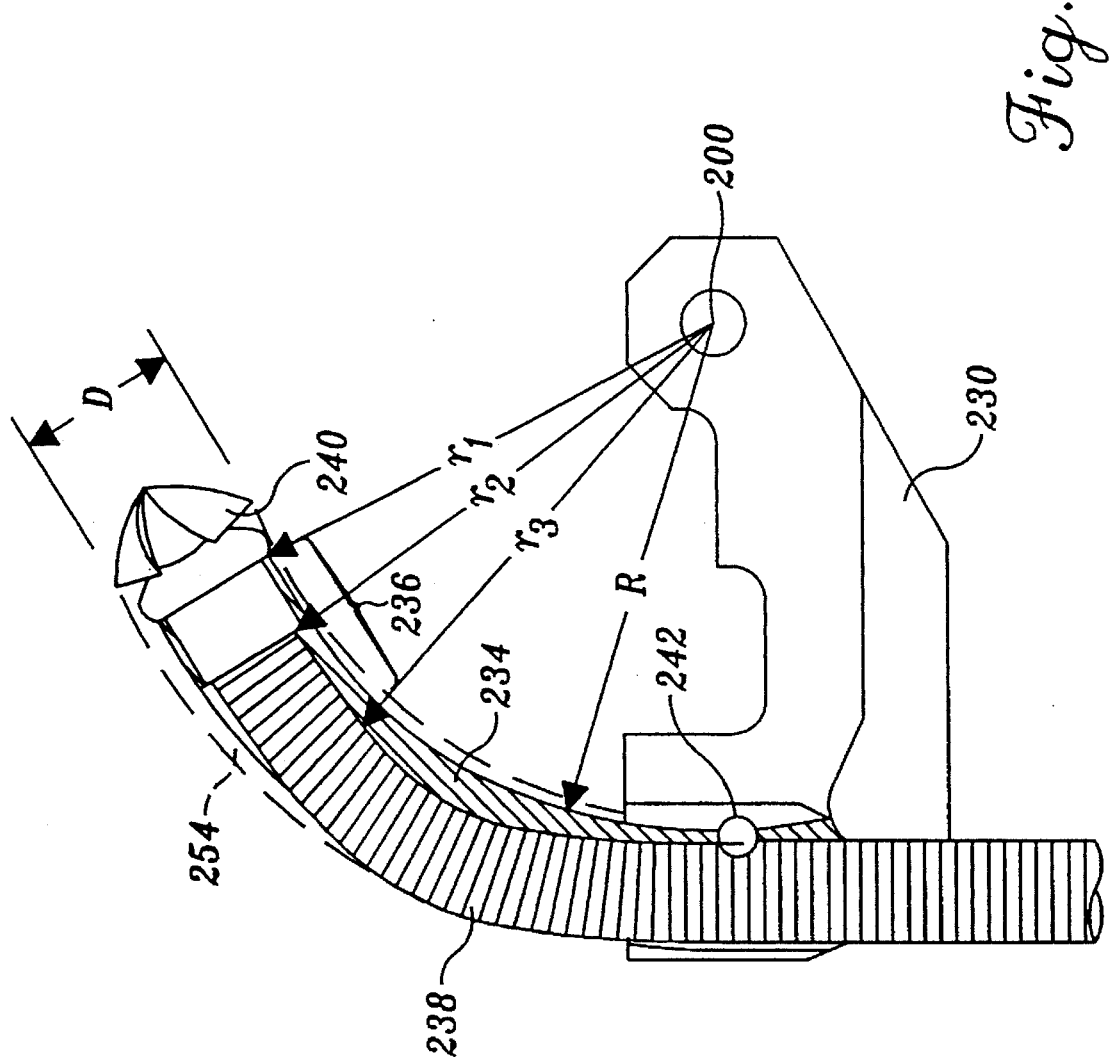

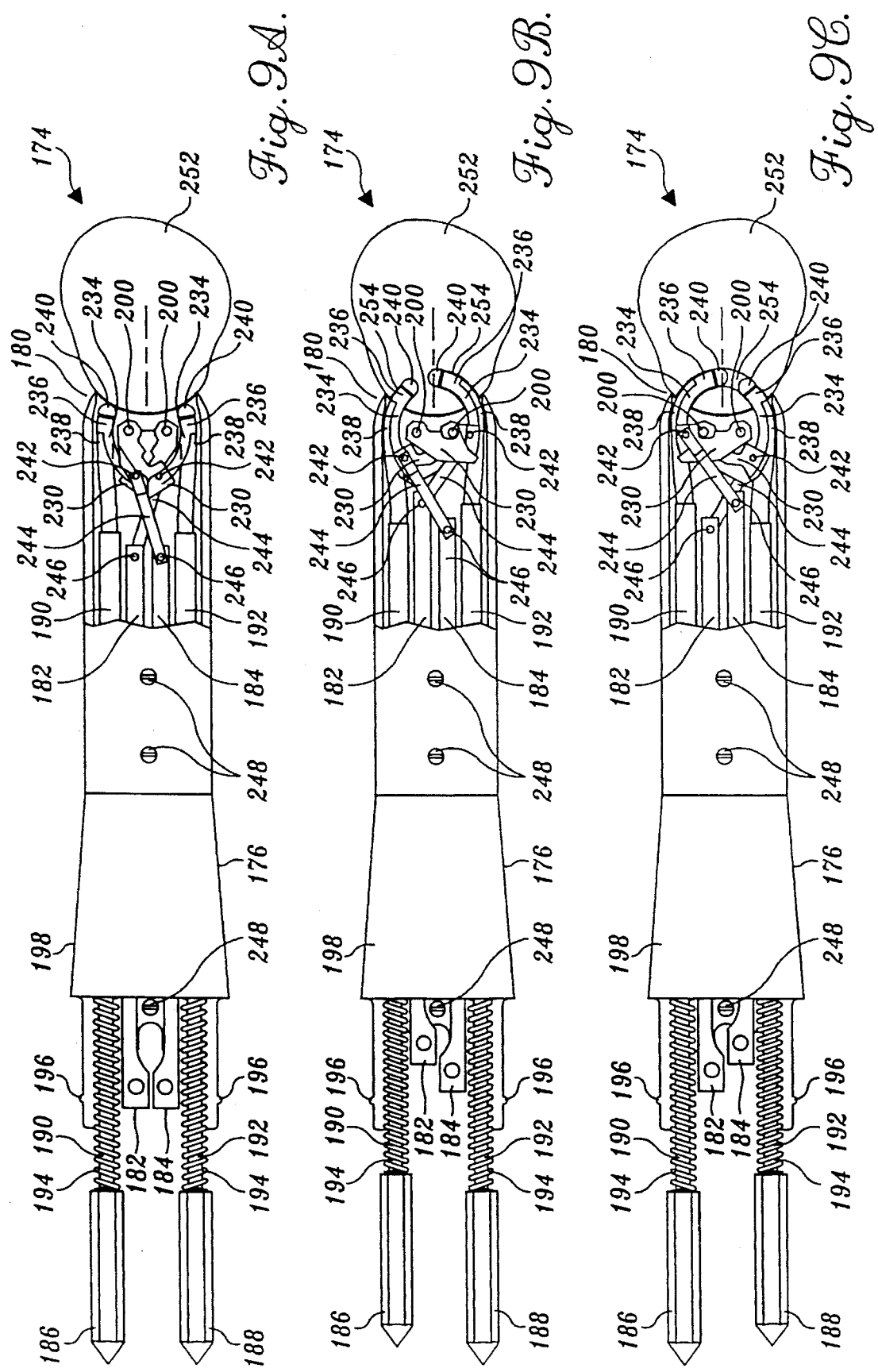

METHOD AND APPARATUS FOR DRILLING A CURVED BORE IN AN OBJECT

FIELD OF THE INVENTION

This invention generally relates to a method and apparatus for drilling a curved bore in an object, and more specifically, to drilling a curved bore using two cutting bits that are advanced through intersecting arcs to form the curved bore in the object.

BACKGROUND OF THE INVENTION

There are many applications in which it is desirable to drill a curved bore in an object. For example, in orthopedic surgery, a number of procedures require a surgeon to secure tissue to bone by using stitches that extend through holes made in the bone; these procedures would benefit greatly if apparatus were commercially available that would allow a curved bore to be efficiently formed in the bone. Instead, the procedure typically employed requires that two angled bores be drilled in the bone, with the hope that the straight bores will intersect so that a curved surgical needle can be forced through the bore without breaking or jamming. To accommodate the curvature of the needle, the straight bores must be larger in diameter than is desired. In addition, there is often limited working space available where the holes must be drilled, making it difficult to maneuver a drill to produce the two straight holes from opposed angles. Of course, there are many industrial processes that would also benefit if low cost apparatus were commercially available that could produce smoothly curved bores in an object. Accordingly, the applications of such apparatus are not in any way limited to the medical field.

A solution to the problem of producing a curved bore is disclosed in two earlier U.S. Pat. Nos. 4,941,466 and 5,002,546, issued to the inventor of the present invention. In the first of these patents, a curved bore drilling apparatus and method are disclosed in which two driven shafts are provided with flexible shaft sections, each having a cutting tip. A semicircular curved drill guide attached to a pivotally mounted swing arm loosely engages and carries each flexible shaft and cutting tip. Two linkage rods couple the drill guides to a push rod that advance the cutting tips so that they simultaneously swing toward each other in intersecting 90° arcs. The push rod is advanced by moving a pivotal handle relative to a stationary handle. In a second embodiment, the drill guides are simultaneously rotated toward each other by a worm and pinion drive actuated by the operator.

U.S. Pat. No. 5,002,546 discloses several different embodiments of apparatus for producing a curved bore using various machining processes in addition to the cutting tips. The apparatus disclosed for supporting the cutting tips and drive mechanism is shaped like a handgun; a trigger is mechanically coupled to various alternative linkages for advancing the cutting means to form the curved bore.

A significant problem with the apparatus for drilling a curved bore disclosed in these two patents relates to an interference between the two cutting tips that occurs when the cutting tips are swung toward each other to meet at about the center of the curved bore. Clearly, it is desirable that the bore be smoothly completed at its center or median point; yet, advancing both cutting tips simultaneously to meet at the center of the bore, as disclosed in this prior art, can cause the two cutting tips to be damaged as their cutting faces rotate against each other and can leave a rough circumferential lip at the median point, because neither cutting tip passes that point. One solution to this problem not disclosed in the prior art patents is to separately advance the cutting tips so that first one crosses over the median point in the bore and is then backed up before the other is advanced past the median point. In this manner, the two cutting tips never contact each other, but both rotate with their curved guide past the median point to complete a smooth curved bore in the object. Since the prior art does not disclose or suggest this technique, it clearly also fails to disclose any mechanism suitable for accomplishing the task.

Using two levers to independently advance the opposed cutting tips through their respective arcs at different times would achieve the desired goal, but is neither a very elegant nor a particularly practical solution to the problem. Ideally, the apparatus for drilling a curved bore should be capable of operation using only one hand, without requiring the user to manipulate separate control levers to advance each cutting tip. Manipulating separate levers to advance the two cutting tips at different times would likely require both hands and would be an unduly complex and difficult operation to repetitively complete, when producing multiple curved bores.

Another issue that is not disclosed in the prior art is the problem and solution for dealing with wear of the flexible drive cables and dulling of the cutting tips that will inevitably occur from time to time. A related issue concerns the need for producing different size and different radius bores without requiring that a different integral drive device be provided for producing each size and radius bore. The design of the apparatus for producing curved bores disclosed in the above-noted references does not readily facilitate replacement of the flexible drive cable and cutting tips, nor does it disclose a mechanism for changing the cutting tips and curved guides as appropriate to produce different size or different radius bores, while continuing to use the same rotational drive and advancement mechanism. Provision for coupling different radii curved guides or different diameter cutting bits housed in removable cartridges with a common drive mechanism offers a cost-efficient solution to this problem.

Because the radius of curvature defined by the path of the bore produced by the apparatus can be relatively small, e.g., less than 0.5 in., the flexible cable driving the cutting bit is forced through a correspondingly small radius of curvature. The point of attachment of the cutting tip or bit to the flexible cable is an area of substantially reduced flexibility in the cable, and unfortunately, is also a point of great stress. It has been observed that any breakage of the flexible cable during use of the curved bore drilling apparatus is more likely to occur adjacent the cutting tip than elsewhere. Accordingly, it is clear that some modification of the prior art apparatus is desirable to extend the useful life of the flexible cable.

SUMMARY OF THE INVENTION

In accordance with the present invention, apparatus for drilling a curved bore in an object include a prime mover for providing a rotational drive force and a pair of flexible cables, each having a proximal end and a distal end. The proximal end is coupled to the prime mover so as to rotate in response to the rotational drive force it provides, and the distal end is coupled to a cutting bit. A housing is provided that also has a distal end and a proximal end, the distal end being positioned adjacent the object in order to drill the curved bore. The flexible cables extend at least part way through the housing. A pair of curved guides are pivotally mounted to rotate in intersecting coplanar arcs and each curved guide supports the distal end of one of the flexible cables. As the pair of curved guides are pivotally rotated outwardly toward each other from the distal end of the housing, they define a path followed by each of the cutting bits as they are rotated to cut the curved bore in an object. The cutting bits are thus supported by the curved guides and rotated by the flexible cables. A pair of levers are pivotally mounted to the housing at pivot pins, and each lever is mechanically coupled to a different one of the curved guides to rotate the curved guide through the coplanar arc when the lever is pivoted about its pivot pin. The levers advance the cutting bits along a common portion of the path at different times to produce the curved bore in the object, so that the cutting bits do not contact each other.

In a first preferred form of the invention, one of the levers comprises a trigger, and means moved by the trigger are provided for pivotally rotating the other lever in first one direction and then in an opposite direction as the trigger is pivoted in only one direction, so that the cutting bits are moved as follows. First, one of the cutting bits is carried past an intermediate point in the path of the bore by the curved guide coupled to the other lever. Next, that cutting bit is then withdrawn from the intermediate point in the path of the bore. Finally, the other cutting bit is carried past the intermediate point to complete the bore, thus avoiding contact between the cutting bits.

The apparatus further includes a control for actuating the prime mover, and the trigger activates the control as the trigger is pivotally moved from a rest position to apply the driving force to advance the cutting bit in order to produce the curved bore hole.

Alternatively, another preferred form of the invention includes a separate trigger, and a linkage mechanically coupling the trigger to both levers. Movement of the trigger in only one direction causes one of the levers to pivotally move in a first direction and then in a second direction that is opposite the first direction, while the other lever moves only in a first direction. The one lever thereby initially advances one of the cutting bits to pivot past an intermediate point in the path of the curved bore, and then to retract along that path as the other cutting bit advances past the intermediate point from the opposite end of the path to complete the curved bore. In one form of this embodiment, the linkage comprises a pair of cams rotatably driven by movement of the trigger. The cams have different surfaces of rotation. Each lever follows the surface of rotation of a different one of the pair of cams, and the shape of a cam determines the movement of the lever tracking along its surface of rotation, so that the movement is different for each lever.

Another form of the immediately preceding embodiment includes linkage that comprise a ramped surface moved by the trigger, which the levers contact at different points. Each lever contacts and moves along a different part of the ramped surface so that movement of the trigger causes the levers to move differently.

Means for adjusting an extent by which pivotal movement of the levers moves the curved guides and the cutting bits are preferably provided to produce curved bore holes of different radii using curved guides of correspondingly different radii. The means for adjusting include a pair of links. Each link extends between one of the curved guides and one of the levers and has an angled portion adjacent the lever that is formed at an angle selected to contact the lever at a defined distance from the pivot pin of the lever. This distance determines a range of pivotal motion of a selected curved guide having a specific radius of curvature.

The housing preferably comprises a handle portion and a removable cartridge portion through which the flexible cables extend. The pair of curved guides are disposed and pivotally mounted in the removable cartridge portion. Disconnectable drive couplings are included to mechanically couple the prime mover to the flexible cables, and disconnectable links mechanically couple the levers to the curved guides. Thus, the removable cartridge and flexible cables can readily be attached and disconnected from the handle and disconnectable drive couplings, respectively. The cartridge portion is sized to engage the handle portion. The disconnectable links each comprise two sections that releasably couple together. Means are provided for unlatching the two sections of the disconnectable links when the cartridge portion is removed from the handle portion of the housing. The disconnectable links each comprise a spring-biased pin on one section of the disconnectable link. Preferably, the means for unlatching comprise a release pin on the handle portion that acts on the spring-biased pin to open the latch for removing the cartridge portion from the handle portion.

Another aspect of the present invention is a method for drilling a curved bore in an object. This method comprises steps that are generally consistent with the functions provided by each of the elements of the apparatus discussed above.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIGS. 2A, 2B, and 2C are top plan views of the handle, with the top of the chamber and barrel cut away to more clearly disclose the relationship of the two cutter guide push rods, with respect to corresponding FIGS. 1A, 1B, and 1C;

FIG. 3A is a side view of part of a handle for a second embodiment of the invention, with one side of a housing of the handle removed to better disclose the components contained therein;

FIG. 3B is a front cutaway view of a portion of the handle of FIG. 3A wherein an internal drive gear is disclosed that accommodates different spacing between drive shafts to facilitate use of the handle to drive cutting bits in removable cartridges designed to produce bore holes of substantially different radii of curvature;

FIG. 4A is a side view of part of a handle for a third embodiment of the invention, with one side of a housing of the handle removed to better disclose the cam advancement components contained therein;

FIG. 4B is a simplified front cutaway view of a portion of the handle shown in FIG. 4A, illustrating the cam advancement mechanism for advancing the cutter guide via movement of push rods;

FIG. 5 is an isometric view of a portion of the barrel and of a removable cartridge that engages the barrel to couple with the drive shafts and push rods used to provide rotational driving motion and to control the advancement of the cutting bits, respectively;

FIG. 7 is a plan view of one of the two opposed curved cutter guides and a flexible cable having a cutting bit attached to one end;

FIGS. 9A, 9B, and 9C are three plan views of the removable cartridge, with the distal portion of the top housing cut away to reveal the differential advancement of the two opposed cutting bits from a rest position (FIG. 9A), at a point where one of the cutting bits is fully advanced past a median point in the bore (FIG. 9B), and then, at a point where the other cutting bit is fully advanced past the median point to complete the bore (FIG. 9C).

DESCRIPTION OF THE PREFERRED EMBODIMENTS

Figure 8:
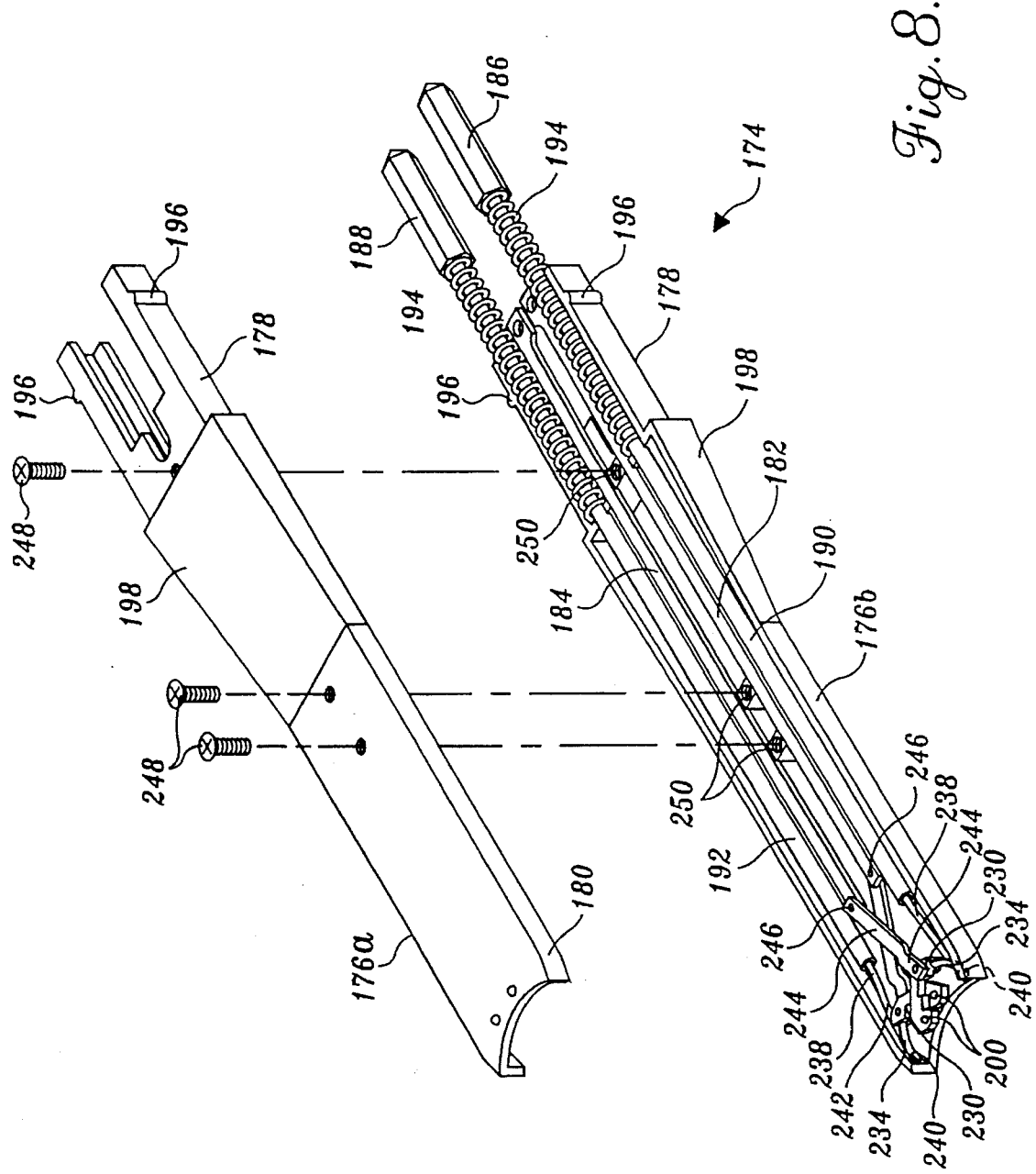
FIG. 8 is an exploded isometric view of the removable cartridge showing the flexible drive cables and other elements of the invention disposed therein.

The apparatus for drilling a curved bore in accordance with the present invention includes a removable cartridge 174 (shown in FIGS. 5, 8, and 9A through 9C), which is used in conjunction with a hand-held drilling energy carrier or drive mechanism. In a first embodiment of this hand-held drive mechanism shown in FIGS. 1A, 1B, and 1C, a handle 20 is illustrated with a left side of a housing 22 removed to disclose the components of the drive mechanism that provide a rotational force to rotate cutting bits 240 (FIG. 8) and also control the advancement of the cutting bits to produce the curved bore—when coupled to removable cartridge 174. Details of the removable cartridge and of the mechanism for pivoting the cutting bits through intersecting arcs to produce the curved bore are disclosed below, following a disclosure of the various embodiments of the handle.

Description of Three Embodiments for the Handle

Figure 1A:
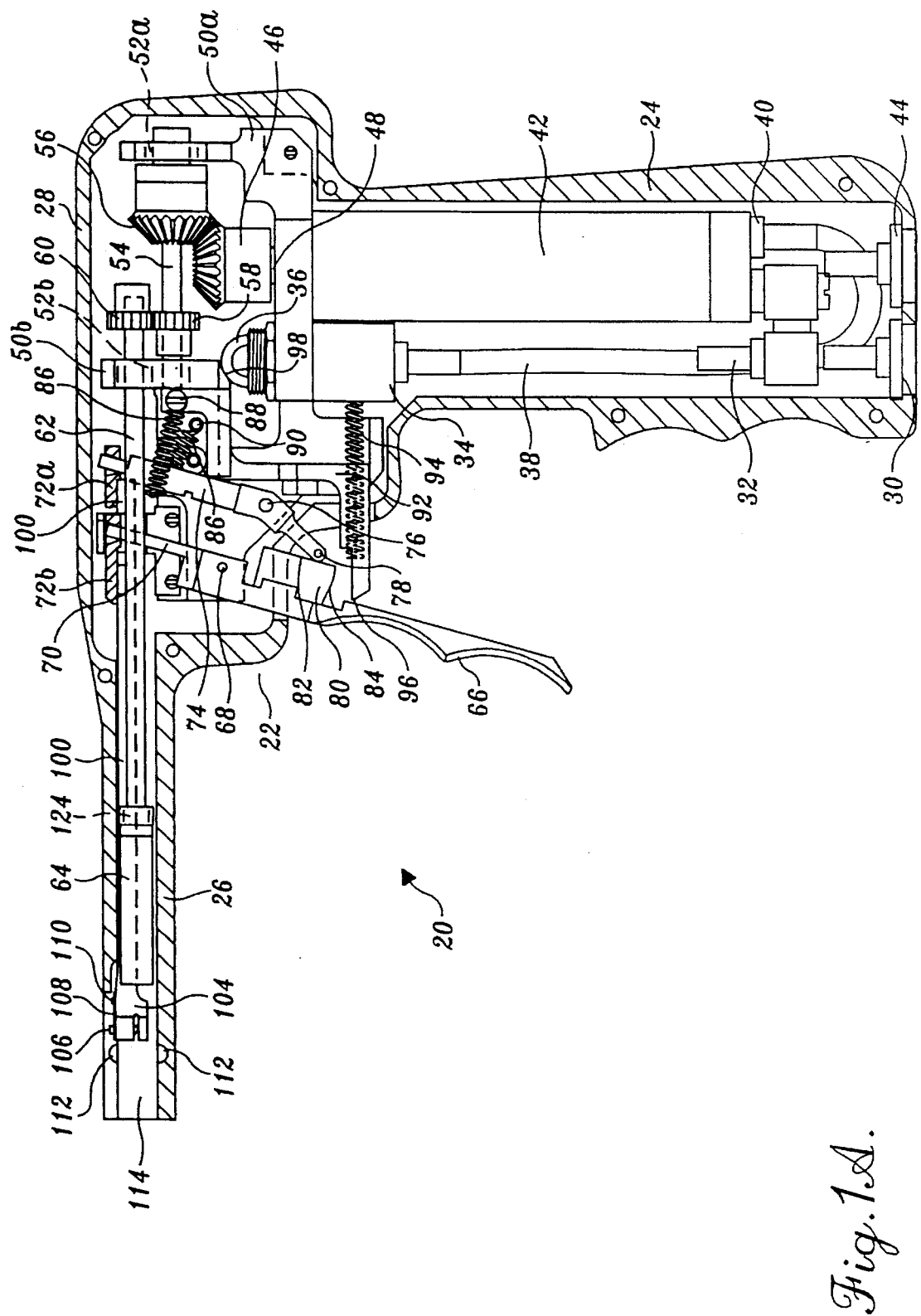
FIGS. 1A, 1B, and 1C are side views of a handle for a first embodiment of the present invention, with one side of a housing of the handle removed in all three views, and the lower portion of the handle cut-away in the latter two views to better disclose the components contained therein, the three views respectively showing a trigger in three successive positions to illustrate the different movement of the two cutter guide push rods in response to rotation of the trigger.

Referring first to FIG. 1A, handle 20 comprises housing 22, of which only the right side is shown. Housing 22 is shaped like a pistol, including a grip 24, a barrel 26, and a chamber 28 in which most of the rotational drive and cutting bit advancement and drive transfer mechanism is disposed. It will be apparent that the left side of housing 22 has been removed in each of FIGS. 1A, 1B, and 1C to more clearly show the components of this mechanism. At the bottom of grip 24 is disposed an inlet port 30, which is adapted to couple to a pneumatic air line fitting (not shown) that supplies pressurized air to handle 20 through a flexible air line connected to an air compressor (neither shown). Inlet port 30 has a fitting 32 that is connected through a line to the inlet of an air valve 34, which is normally closed to interrupt air flow to the outlet of the air valve. At the top of air valve 34 is disposed a valve stem 36, having a general dome shape configuration, which facilitates depression of the valve stem to open air valve 34. When valve stem 36 is depressed into the body of air valve 34, pressurized air flows from the inlet, through the air valve, and from the outlet through a line 38 into a motor inlet port 40. To better illustrate the disposition of line 38, the line between fitting 32 and the inlet of air valve 34 has been removed in these figures. The pressurized air energizes a pneumatic motor 42, causing a drive shaft 48 to rotate. It will be understood that an electric motor, hydraulic motor, or other type of prime mover could alternatively be employed to rotate drive shaft 48. Drive shaft 48 extends upwardly from the top of pneumatic motor 42 and is coupled to rotate a bevel gear 46.

A mounting bracket 50a supports pneumatic motor 42 and air valve 34 within grip 24. In addition, in chamber 28, mounting bracket 50a supports a bearing 52a in which one end of an idler shaft 54 turns. The opposite end of idler shaft 54 is supported by a bearing 52b within a mounting bracket 50b that is attached to housing 22.

Bevel gear 46 engages a bevel gear 56 that is coupled to idler shaft 54, causing the idler shaft to rotate when pneumatic motor 42 is energized with pressurized air. Air at a relatively lower pressure and higher volume than that applied to motor inlet port 40 exits pneumatic motor 42 through a muffler outlet port 44, which is disposed at the base of grip 24. Although not shown, a conventional pneumatic muffler is readily connected to muffler outlet port 44 to substantially silence the flow of exhaust air from pneumatic motor 42.

As idler shaft 54 rotates, a drive gear 58 that is connected to the idler shaft between bearings 52a and 52b also rotates. Drive gear 58 meshes with a left driven gear 60 and with a right driven gear 118 (as more clearly shown in FIGS. 2A, 2B, and 2C). Mounting bracket 50b also supports a left drive shaft 62 to which left driven gear 60 is attached. Left drive shaft 62 extends through barrel 26, and a left drive coupling 64 is connected to left drive shaft 62 adjacent the distal end of the barrel. Similarly, a right drive shaft 120 is supported by mounting bracket 50b and is rotated by right driven gear 118. Right drive shaft 120 extends through the barrel and is connected to a right drive coupling 122 adjacent the distal end of barrel 26. Both left drive shaft 62 and right drive shaft 120 are supported by a bearing block 124 at about the midpoint position along the length of the barrel.

Figure 1B:
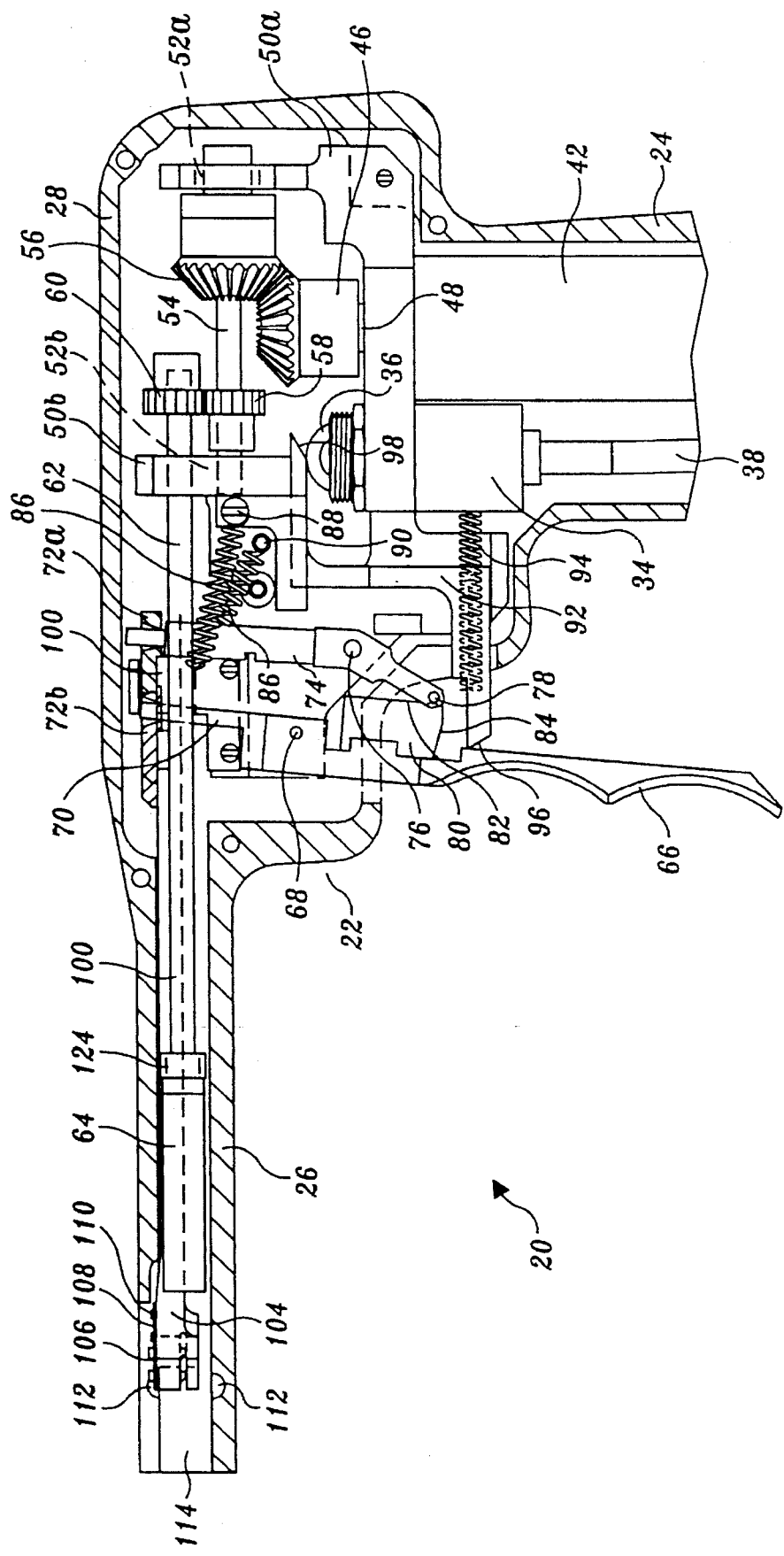
Figure 1C:
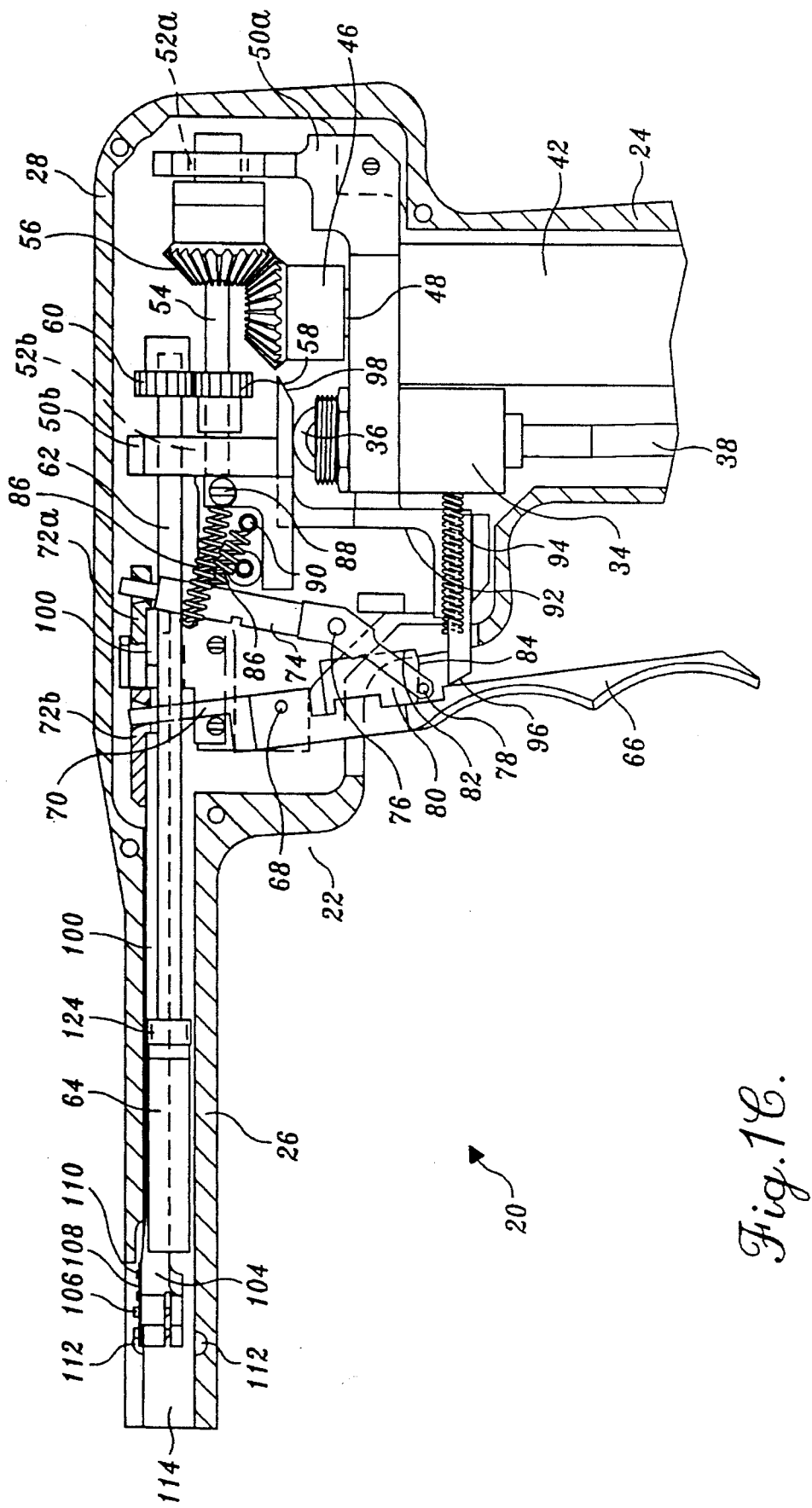

A trigger 66 is mounted to housing 22 at a pivot pin 68 so that as the trigger is squeezed by the fingers of a user toward grip 24, the trigger rotates about pivot pin 68, moving an upwardly extending lever portion 70 of trigger 66 in a short arc. Lever portion 70 engages a link 72b, which is attached to a right push rod 102. In addition, as trigger 66 is squeezed toward grip 24, a lever 74 disposed behind the trigger is rotated about a pivot pin 76. The lower end of lever 74 includes a roller 78, which rides on a cam block 80. Cam block 80 is attached to the back side of trigger 66 and includes two surfaces over which roller 78 rides, including an "advance" surface 82 and a "fall-off" surface 84, the significance of which will shortly be evident. The upper end of lever 74 engages a link 72a, which is connected to a left push rod 100 (only a small portion of which is shown in FIGS. 1A–1C). Left push rod 100 also extends through barrel 26, toward its distal end, generally parallel to right push rod 102. Bearing block 124 is relieved along its top surface to provide clearance and support for the left and right push rods, which extend beyond the bearing block.

To provide a biasing force that tends to resist rotation of lever 74 when trigger 66 is squeezed toward grip 24, a helical coiled spring 86 is looped around a front edge of lever 74, extending between a bolt 88 and a bolt 90 that secure the ends of the spring to mounting bracket 50b. A biasing force that resists squeezing and pivotal movement of trigger 66 is provided by a helical coil spring 94, which extends from the rear of a valve actuator slide 92 to the front surface of air valve 34. Valve actuator slide 92 has a zigzag shape, extending from a tip 96 on its lower portion to a tip 98, which abuts against valve stem 36. As trigger 66 is initially squeezed toward grip 24, the rear surface of the trigger contacts tip 96, valve actuator slide 92 compresses helical coiled spring 94, and tip 98 depresses valve stem 36, enabling pressurized air flow through air valve 34.

At substantially the same time that movement of trigger 66 opens air valve 34 to energize pneumatic motor 42, the ramped slope defined by advance surface 82 on cam block 80 acts on roller 78, causing lever 74 to rotate about pivot pin 76 and advancing link 72b and left push rod 100 to which it is connected from their normal rest positions, to more forward positions, i.e., moving left push rod 100 toward the distal end of barrel 26. As trigger 66 is initially squeezed toward grip 24, lever 74 rotates about pivot pin 76 to move left push rod 100 sooner and to a greater extent than upwardly extending lever portion 70 rotating about pivot pin 68 initially moves right push rod 102. Thus, left push rod 100 advances more rapidly than right push rod 102.

Referring now to FIG. 1B and corresponding FIG. 2B, the relationship between the left and right push rods 100 and 102 due to rotation of upwardly extending lever portion 70 and lever 74 is clearly illustrated. At the intermediate point in the rotation of trigger 66 represented if FIG. 1B, roller 78 on the lower end of lever 74 is disposed at the very end of advance surface 82 on cam block 80. Left push rod 100 has advanced a left clip 104 that is attached to the left push rod adjacent an opening 114 at the distal end of barrel 26 to about a maximum displacement (shown in FIG. 2A) relative to its original rest position. As will become apparent during the discussion of the removable cartridge that is coupled to barrel 26 and as shown in FIGS. 9A through 9C, the displacement of left clip 104 shown in FIG. 2B corresponds to pivoting of cutting bit 240, which is disposed on the right in the removable cartridge, past a median point in a curved bore 254 being formed in an object 252. To complete the curved bore, it is necessary for the opposed cutting bit on the left to subsequently also be advanced past the median point, thereby creating a clean curved bore without any circumferential lip at the medium, as would result if both the cutting bits were simultaneously advanced to meet at the median point in the bore.

To avoid interference between the linkage and damage to the two cutting bits 240 that would occur if they contacted each other, left clip 104 must be retracted from its maximum displaced position shown in FIG. 2B before right clip 116 is advanced to a point of maximum displacement, as shown in FIG. 2C. FIG. 2C corresponds to the fully rotated position of trigger 66 shown in FIG. 1C. It will be noted in FIG. 1C that roller 78 on the lower portion of lever 74 has moved from advance surface 82, dropping onto fall-off surface 84, thereby allowing lever 74 to move in a retrograde direction relative to its initial movement that occurred when trigger 66 was initially squeezed toward grip 24. As a result of the retrograde motion of lever 74, left clip 104, as shown clearly in FIG. 2C, has moved behind the point of maximum displacement of right clip 116. Since left clip 104 and right clip 116 are advanced at different rates and do not reach a maximum forward displacement simultaneously, interference between the cutting bits in a removable cartridge to which they are coupled is avoided.

A second embodiment of a handle 20' is shown in FIG. 3A. Any of the components of the present invention associated with handle 20' that are identical in function and form to those discussed above in regard to handle 20 have the same reference numerals. However, those elements associated with handle 20' that have the same function but different form or configuration from those of handle 20 include a prime designation in their reference number. Thus for example, a housing 22', which is different in shape than housing 22, is used in connection with handle 20'; a chamber 28' has a slightly larger volume than chamber 28 to accommodate a bevel internal gear 56'.

Bevel internal gear 56' is mounted and supported to freely turn within a bearing 52', which in turn, is supported by a mounting bracket 50a'. Bevel internal gear 56' meshes with and is driven by bevel gear 46.

As shown in FIG. 3B, a left driven gear 60' is attached to the end of a left drive shaft 62' (although appearing on the right in the view of FIG. 3B) and is drivingly rotated by bevel internal gear 56'. Similarly, a right drive shaft 120', having a right driven gear 118 mounted on its end is also drivingly rotated by bevel internal gear 56'. One of the advantages of bevel internal gear 56' over bevel internal gear 56 in the first embodiment, is its ability to apply rotational force to left and right drive shafts that are spaced apart in varying degree, and thereby, to accommodate removable cartridges configured to produce curved bore holes of significantly different radii. For example, as shown in phantom view, left and right gears 146 and 148 are mounted to engage bevel internal gear 56' at a substantially wider spacing (exaggerated) than left and right driven gears 60' and 118'. Although a limited variation in the radii of the curved bore made with different cartridges (e.g., ±0.2 in.) can be accommodated without changing the spacing between the left and right drive shafts, more significant changes in radii require wider bodied removable cartridges that are designed to couple with more widely spaced left and right drive shafts. Small variations in the vertical position of left and right drive shafts 62' and 120' that occurs when the spacing between them is changed are readily accommodated within the space allocated inside barrel 26 of handle 20'.

Referring to FIG. 3A, it will be apparent that a different advancement mechanism is used to control the advancement of a left push rod 100' and a similar right push rod (not shown). Specifically, in this embodiment, a trigger 66' is mounted to pivotally rotate about a pivot pin 68'. However, unlike trigger 66, which was used in handle 20 (shown in FIG. 1A through FIG. 1C), trigger 66' does not directly advance one of the push rods. Instead, a left lever 134 and a corresponding right lever 142 are provided to couple the rotational motion of trigger 66 into the advancement of the left and right push rods. Only the lower portion of right lever 142 is shown in FIG. 3A, since it is hidden behind left lever 134 over most of its length; however, although shorter at its lower end below pivot pin 138, right lever 142 is otherwise substantially identical to left lever 134. The lower end of right lever 142 includes a roller 144. Similarly, the lower end of left lever 134 includes a roller 140 that rides along cam block 80 ahead of roller 144. As a result, left lever 134 advances left push rod 100' to its maximum displaced position before right lever 142 advances the other push rod to that extent. Thereafter, roller 140 drops onto fall-off surface 84 on cam block 80, allowing left push rod 100 to move in a retrograde motion relative to its initial advancement. However, roller 144 continues to roll along the advance surface of cam block 80 until the other push rod to which it is coupled has reached its maximum forward displacement. It should be noted that separate cam blocks can alternatively be attached to the back of trigger 66' for rollers 140 and 142, independently controlling the rate at which the left and right levers pivotally rotate.

A helical coil spring 86' provides a biasing force that resists the forward rotation of the upper portion of left and right levers 134 and 142. Simultaneously with the rotational movement of trigger 66' to initially advance push rod 100', valve actuator slide 92 depresses valve stem 36, opening air valve 34. Thus, in handle 20', squeezing trigger 66' has substantially the same net effect in terms of advancing first one cutting bit and then the other past a median point in the circular bore while pressurized air is applied to energize pneumatic motor 42 and thus to provide rotational force to rotate the cutting bits.

To further accommodate removable cartridges designed to produce bores of substantially different radii, the left and right push rods are coupled to separate adjustable links 130 (only one visible in FIG. 3A), which can be positioned at different points along the length of left and right levers 134 and 142. The surface of these two levers that contacts the end of adjustable link 130 includes a series of notches 136 to accommodate positioning the adjustable link so that the same relative angular movement of left and right levers 134 and 142 results in a different displacement of the two push rods. For example, adjustable link 130 is shown in a position 132 in phantom view that would produce a substantially greater displacement of the left push rod for a given rotation of the trigger 66'. The greater advancement of the push rods for a given angular displacement of the levers thus achieved may be required for a removable cartridge designed to produce a circular bore having a substantially greater radius compared to that which would be produced by the removable cartridge coupled to handle 20', with adjustable link 130 placed in the (non-phantom) position shown in FIG. 3A. Inclusion of adjustable link 130 thus enables handle 20' to be configured for advancing the cutting bits in removable cartridges by varying degrees, to produce curved bores of substantially different radii, thereby eliminating the need to provide completely different configuration handles for each removable cartridge designed to produce bore holes of different radii of curvature.

A third embodiment for the handle is shown generally at reference numeral 20' in FIG. 4A. FIG. 4B shows a cutaway view of handle 20', viewed from just behind a trigger 66'. Again, reference numerals that are common to the first embodiment shown in FIGS. 1A–1C are used for identical elements, and primes are added to reference numerals of elements having common functions but different configurations. For example, trigger 66' pivots about a pivot pin 68', but does not include a cam block 80 as did the triggers in the first two embodiments. Instead, the rear surface of trigger 66' contacts a tip 96' on a valve actuator slide 92' as the trigger is squeezed toward grip 24. Movement of valve actuator slide 92' again causes tip 98 to depress valve stem 36, opening air valve 34 to provide pressurized air to energize pneumatic motor 42. At the same time, valve actuator slide 92' rotates a pinion gear 152, which meshes with a gear rack 150 formed on the upper surface of valve actuator slide 92'.

As shown more clearly in FIG. 4B, pinion gear 152 is attached to a shaft 154 that extends between opposite sides of housing 22 and is rotatably driven by the gear. A left cam 156 is disposed on the left side of valve actuator slide 92 and a right cam 158 on the other side. Rotation of pinion gear 152 occurring when a user squeezes trigger 66' rotates left and right cams 156 and 158 in a counterclockwise direction, as shown in FIG. 4A.

Left cam 156 preferably has a different shape than right cam 158 to ensure that left push rod 100 is advanced to its maximum displacement before right push rod 102, and then moves in an opposite direction. Alternatively, the left and right cams can have the same shape, but be mounted at different rotational positions on shaft 154. A left lever 160 rides along the surface of rotation of left cam 156 as it rotates so that the relative change in radius of the left cam produces a corresponding rotation of left lever 160 about a pivot pin 138'.

Similarly, a right lever 162 rides on the surface of rotation of right cam 158 as it rotates, advancing link 72b and its connected right push rod 102 to a point of maximum displacement after push rod 100 has begun a retrograde motion to pull back from its point of maximum displacement. Helical springs 164 apply a bias force that resists rotation of left and right levers 160 and 162 to advance link 72a and 72b, respectively. Once again, the differential movement of the left and right push rods avoids interference between opposed cutting bits in the removable cartridge as the bits are swung in an arc to form the curved bore.

Description of the Removable Cartridge and Its Engagement with Handle

FIG. 5 illustrates a portion of barrel 26 and removable cartridge 174 that is positioned to engage the barrel. The removable cartridge comprises a housing 176 that comprises a top 176a and a bottom 176b, held together with threaded fasteners 148 that mate with threaded holes 150 in bottom 176b. Alternatively, the top and bottom of housing 176 can be adhesively or ultrasonically bonded together. Housing 176 has a proximal end 178, a flared shoulder 198 that is adjacent the proximal end, and a distal end 180, within which are disposed the opposed cutting bits. The opening of distal end 180 of the removable cartridge defines a concave curve suitable for placement against a rounded object into which the curved bore is to be formed. Proximal end 178 is sized and shaped to fit within opening 114 at the distal end of barrel 26.

Inside opening 114 at the distal end of barrel 26, left drive coupling 64 includes a relieved opening 170 having an internal regular hexagonal configuration to mate with a corresponding left hexagonal fitting 186 that extends from the distal end of the removable cartridge. Similarly, a right hexagonal fitting 188 mates with right drive coupling 122, which is disposed at the end of right drive shaft 120. Relieved openings 170 in both the left and right drive couplings and a rounded tip on left and right hexagonal fittings 186 and 188 ensures that the hexagonal fittings readily slide into the relieved openings and engage the drive couplings. The left and right hexagonal fittings are connected to extended left and right drive shafts 190 and 192 that run in substantially parallel alignment through the length of the removable cartridge. Helical coil springs 194 that are concentric around the left and right extended drive shafts at proximal end 178 provide a biasing force tending to maintain the left and right hexagonal fittings in a rearwardly extending position, i.e., extending outwardly from proximal end 178 of removable cartridge 174. Flared shoulder 198 is intended to abut against the distal end of barrel 26 as proximal end 178 is slidably engaged within opening 114 of the barrel.

Between the left and right extended drive shafts 190 and 192 in the removable cartridge are disposed left and right push bars 182 and 184, respectively. Left and right push bars 182 and 184 are adapted to couple to corresponding left and right clips 104 and 116, which are disposed in barrel 26 at the distal ends of left push rods 100 and right push rod 102, respectively. Specifically, left and right push bars 182 and 184 slide into slots 172 formed within the left and right clips and are engaged by retainer pins 106. Grooves 112, formed internally, on the sides of barrel 26 also engage ridges 196 formed along each side of proximal end 178 of removable cartridge 174, in a friction fit. It will be apparent that the disposition of the grooves and ridges can be interchanged, so that the grooves are formed on the sides of the proximal end of removable cartridge 174 and the ridges are formed internally on the sides of barrel 26. When the proximal end of removable cartridge 174 is inserted within opening 114 on barrel 26, the rotational drive force conveyed through both the left and right drive shafts are coupled via the left and right drive couplings to the extended left and right drive shafts through the hexagonal fittings. The force used to advance the cutting bits is coupled from left and right push rods 100 and 102 into left and right push bars 182 and 184 as the push bars engage left and right clips 104 and 116. As the left and right push bars move, the hexagonal fitting slides longitudinally inside the drive couplings.

Figure 6A:
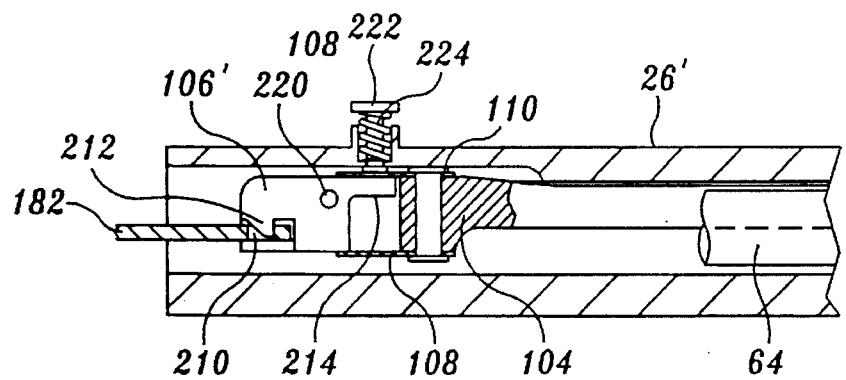
FIGS. 6A and 6B are simplified side views of an end of the barrel, with the side of the barrel partially cut away and a proximal end of the cartridge removed to more clearly show a preferred embodiment for releasable clips (only one shown) that couple push rods in the barrel with push bars in the cartridge.
Figure 6B:
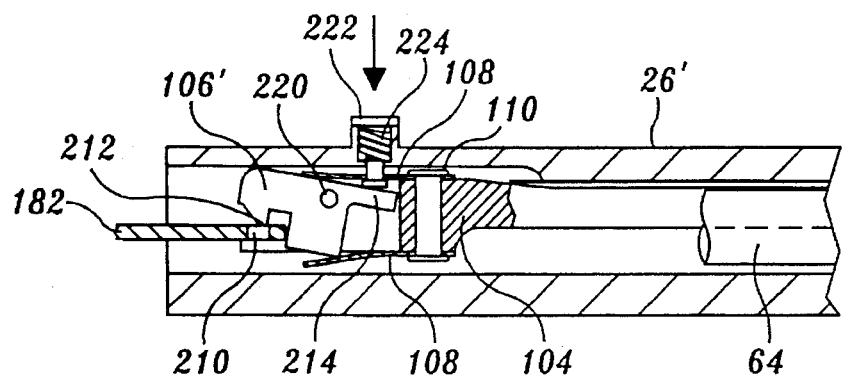

Details of a preferred embodiment for left and right clips 104 and 116 are shown in FIGS. 6A and 6B. In addition, an alternative embodiment of a barrel 26' is illustrated that includes a release button 222, which facilitates releasing a retainer pin 106' from an aperture 210 formed in left push bar 182. A corresponding aperture 210 is formed in right push bar 184, which is not visible in FIGS. 6A and 6B. Release button 222 is generally H-shaped and is mounted on barrel 26' and biased outwardly by a pair of helical coil springs 224 (only one of which is shown) that are concentric with the two depending stems of the release button. The lower ends of these stems on release button 222 are flattened to ensure their retention inside barrel 26'.

In FIG. 6A, details of left clip 104 (partially cut away) are shown. Left clip 104 includes a rivet 110 that extends vertically through the clip to attach flexures 108 to the top and bottom of the clip. A pivot pin 220 extends between opposed sides of the clip, pivotally supporting retainer pin 106'. Flexures 108 provide a bias force that tends to keep retainer pin 106' in the position shown in FIG. 6A, so that a tang 212 on the retainer pin engages aperture 210 when the removable cartridge is engaged in the end of barrel 26'. To facilitate removal of the cartridge, release button 222 is depressed by the user as shown by the arrow in FIG. 6B. When thus depressed, the lower end of one of the stems on release button 222 forces a lever arm 214 of the retainer pin to pivot downwardly about pivot pin 220, against the biasing force developed by deflection of flexures 108. This rotational movement of the retainer pin causes tangs 212 to withdraw from apertures 210, easing the disengagement of the removable cartridge from barrel 26'. Alternatively, with respect to barrel 26, tangs 212 on retainer pins 106 have a rounded dome shape and the apertures that they engage on the ends of the left and right push bars can be formed as open slots, facilitating disengagement of push bars 182 and 184 from left and right clips 104 and 116, respectively, simply by pulling the removable cartridge to extract it from barrel 26 with sufficient force to overcome the biasing force of flexures 108.

Figure 6C:
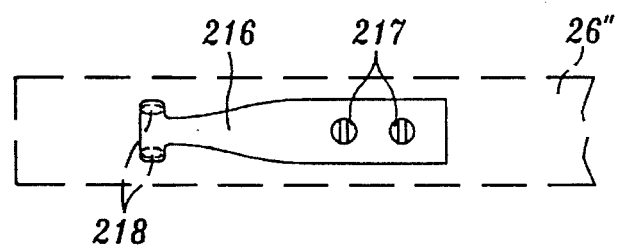
FIG. 6C shows a plan view of an alternative embodiment for a release mechanism adapted to be fitted to the barrel (shown in phantom view) to actuate the releasable clips.
Figure 6D:
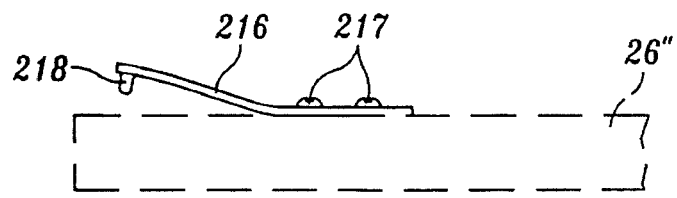
FIG. 6D is a side elevational view of the release mechanism of FIG. 6C, showing how it is mounted on the barrel (a portion of which is shown in phantom view)

FIGS. 6C and 6D illustrate an alternative to release button 222 in which a flexure release lever 216 stamped from sheet metal has two downwardly depending tabs 218 at one end that are sized to act on lever arms 214 of retainer pins 106' when the upwardly extending end of the flexure release lever is depressed by the user. When thus depressed, downwardly depending tabs 218 cause retainer pins 106' pivot so that tangs 212 are withdrawn from apertures 210. The removable cartridge can then be readily withdrawn from a barrel 26' (shown in phantom view) to which the flexure release lever is fastened with threaded fasteners 217. Spring bias force in the flexure release lever restores it to the position where it suspended above the top of barrel 26'. Flexure release lever 216 is a lower cost, simpler design than release button 222, but equally effective in accomplishing the task of releasing the left and right push bars of the removable cartridge from the left and right push rods in the barrel.

Description of the Components Inside the Removable Cartridge

Details of an exemplary swing arm 230 and curved guide arm 234 are shown in FIG. 7. Identical swing arms 230 and guide arms 234 are provided for both of the opposed cutting bits 240, but the guide arm for one of the cutting bits is inverted when mounted at distal end 180 of the removable cartridge. Swing arm 230 includes one of the two pivot pins 200, which is used to pivotally mount the swing arm at the distal end of removable cartridge 174. A constant radius of curvature R defines the distance between the center of pivot pin 200 and the exterior surface of the curved guide arm, along the inside circumference of its curvature about pivot pin 200. However, the radius between the center of pivot pin 200 and the internal circumferential surface of the curved guide arm against which the flexible drive cable is guided, is not constant. Instead, the inner wall thickness of the curved guide arm varies of the length of its curve, causing the radius between the internal surface and the center of pivot pin 200 to vary accordingly, as explained below. The cutting bits produce a curved bore 254 having a radius of curvature that is slightly different than (R+D/2), where D is the diameter of the cutting bit, because of the separation between the centers of the two pivot pins 200 and because the pivot pins are necessarily set back from the inside curve at the distal end of the removable cartridge.

Each cutting bit 240 is soldered or otherwise fastened to a flexible drive cable 238 that conveys a rotational drive force to the cutting bit from one of the left or right extended drive shafts 190 or 192 to which the other end of the flexible drive cable is attached. As each curved guide arm 234 is pivoted outwardly from distal end 180 in a coplanar arc with the other curved guide arm, the cutting bit produces a curved bore having a diameter D that is greater than the diameter of curved guide arm 234 with flexible drive cable 238 in place. The flexible drive cable is constrained on the inside of its curved path by curved guide arm 234 and on the outside of the curved path by the bore that the cutting bit is producing. The larger diameter of cutting bit 240 provides the clearance required for flexible drive cable 238 and curved guide arm 234 to advance freely through the bore behind the cutting bit. Cutting bit 240 is loosely supported and carried with curved guide arm 234 during its pivotal rotation about one of pivot pins 200, so that the flexible drive cable wraps around the curved guide arm through the arc of its travel. This arc intersects the arc formed by the other curved guide arm and the partial bore that the other cutting bit produces to complete the curved bore since the two arcs are coplanar. However, each curved guide arm is swung outward beyond a median point within the bore hole at a different time by the mechanism in handles 20, 20' or 20", so that the opposed cutting bits do not contact each other.

As noted above in the Background of the Invention, one of the problems recognized with the prior art design for producing a curved bore hole using two opposed cutting bits is the problem of breakage incurred in the flexible drive cable, particularly at the point where the cutting bit attaches to the flexible drive cable. Since left drive shaft 62, right drive shaft 120, and left and right extended shafts 190 and 192 are solid, they have considerably greater resistance to breakage than does flexible drive cable 238, which comprises a plurality of wire strands and is generally of very small diameter, e.g., less than 0.05 in. In particular, it has been determined that the flexible drive 238 cable has a substantially reduced flexibility in the vicinity where cutting bit 240 is attached to the flexible drive cable, i.e., just behind the cutting bit; therefore, it is important to avoid flexure of flexible drive cables 238 in this region. Accordingly, curved guide arm 234 is curved along substantially its entire length, except at the end adjacent cutting bit 240, where it includes a relatively short, substantially straight segment 236. The distal end of straight segment 236 extends around the shank of cutting bit 240 and serves as a thrust bearing for the cutting bit. To provide the straight segment, the wall thickness of curved guide arm 234 along the inner circumference is slightly relieved or tapered along its curved length. It is this tapering of the wall thickness that causes the variation in the radius between pivot pin 200 and the inside surface of the curved guide arm. For example, this radius is equal to $r_1$ at the bearing portion of straight segment 236, changes to $r_2$ behind the bearing portion, and is equal to $r_3$ at the beginning of the straight segment, where $r_1$, $r_2$, and $r_3$ are all unequal radii. Straight segment 236 thus avoids flexure of flexible drive cable 238 where it attaches to the cutting bit, since the flexible drive cable is least able to handle the stress at this point, and shifts the flexure to a portion of the flexible drive cable proximal of the straight segment, where the flexible drive cable can better withstand the stress, thereby reducing the likelihood of flexible drive cable breakage. It will be apparent that an alternative curved guide arm (not shown) having constant thickness wall, e.g., a metal stamped part, could also be used, if formed to provide a substantially straight segment adjacent the cutting bit.

Preferably, housing 176 of removable cartridge 174 is formed of a low-cost injection molded plastic. Since it is virtually impossible to economically sterilize removable cartridge 174 after use in a surgical procedure to produce one or more curved bores in the bone of a patient undergoing the surgical procedure, it is important that removable cartridge 174 be of low cost and designed to be discarded after use with a single patient. For this reason, it is important that the removable cartridge be made of inexpensive materials and easily engaged with handle 20, 20', or 20", so that the removable cartridge can be readily replaced. These criteria are also likely to be important in industrial applications.

FIG. 8 and FIGS. 9A through 9C disclose further details of removable cartridge 174. For example, in FIG. 8, an exploded view illustrates a bottom housing 176b through which left and right extended drive shafts 188 and 190 convey rotational force from the proximal to distal ends of the removable cartridge. The ends of the left and right extended shafts are coupled to flexible drive cables 238, which convey the rotational force to cutting bits 240. Left push bar 182 is coupled to a push link 244 to convey the force to advance cutting bit 240 by pivoting one of swing arms 230 and the curved guide arm that supports the cutting bit in an arc about pivot pin 200. Similarly, right push bar 184 is coupled to another push link 244, which conveys the force to advance the other swing arm 230 and the other curved guide arm that supports the other cutting bit 240 in an arc to form the other part of the bore in an object. Each push link 244 is formed with an offset between the part of the push link that pivots about a pivot pin 242 at swing arm 230 and the part that pivots about a pivot pin 246 at the left or right push bar 182 or 184. The offset in push links 244 provide clearance relative to swing arms 230 as the two swing arms are pivoted outwardly about pivot pins 200 to produce the curved bore with the cutting bits.

Turning now to FIGS. 9A, 9B, and 9C, the relative positions of the two opposed cutting bits 240 are illustrated as they would appear at successive times during the formation of curved bore 254 in an object 252. The cutting bits are shown in a rest position in FIG. 9A, before a user begins squeezing the trigger against the grip on the handle. In FIG. 9B, the trigger has moved part way through its complete range of travel, causing left push bar 182 to advance from its rest position. Displacement of the left push bar is transmitted through push link 244, which is connected between that push bar and swing arm 230, so that cutting bit 240 is pivoted outwardly by the curved guide arm to cut a partial curved bore that extends past a median point in the completed curved bore to be formed in object 252. (The median point is indicated by the dash line.) The object is abutted against distal end 180 of removable cartridge 174. Further movement of the trigger produces retrograde displacement of left push bar 182, causing the cutting bit 240 on the right, which is supported by the swing arm coupled to the left push bar, to withdraw back away from the median point in the bore as right push bar 184 continues to advance the other swing arm 230 and curved guide arm on the left. Further advancement of push bar 184 advances the other cutting bit past the median point to complete curved bore 254 in object 252. When the trigger is released, both cutting bits 240 return to their normal rest position as shown in FIG. 9A. Accordingly, the present invention produces curved bore 254 within object 252 without risk of cutting bits 240 contacting each other, and the curved bore is substantially smoother than would be the case if neither cutting bit had passed the median point.

While the present invention has been disclosed with respect to several preferred embodiments, those of ordinary skill in the art will appreciate that further changes to the invention can be made within the scope of the claims that follow. Accordingly, it is not intended that the scope of the invention be in any way limited by the disclosure of the preferred embodiments set forth above, but instead that it be determined entirely by reference to the claims.

The embodiments of the invention in which an exclusive property or privilege

1. Apparatus for drilling a curved bore, comprising:
    (a) a prime mover for providing a rotational drive force;
    (b) a pair of flexible cables, each flexible cable having a proximal end that is mechanically coupled to the prime mover so as to rotate in response to the rotational drive force and a distal end coupled to a cutting bit;
    (c) a housing through which the flexible cables extend, said housing having a distal end;
    (d) a pair of curved guides that are pivotally mounted to swing relative to the housing in coplanar arcs that intersect at a location fixed relative to the housing, each curved guide supporting the distal end of one of the flexible cables, so that as said pair of curved guides are swung outwardly toward each other from the distal end of the housing, they define a continuous composite path defined by the cutting bits as they are swung relative to the housing to bore the curved bore, said cutting bits being supported by the curved guides and rotated by the flexible cables; and (e) a pair of levers, each lever being pivotally mounted to the housing at a pivot pin and mechanically coupled to a different one of the curved guides to swing that curved guide through the coplanar arc when the lever is pivoted about its pivot pin; and (f) means for controlling movement of said levers so as to advance the cutting bits relative to the housing along a common portion of the path at different times, to produce the curved bore without the cutting bits contacting each other.

2. The apparatus of claim 1, wherein one of the levers comprises a trigger, the controlling means including means moved by the trigger for pivotally swinging the other lever relative to the housing in first one direction and then in an opposite direction as the trigger is pivoted in only one direction, so that:

(a) one of the cutting bits is moved relative to the housing past an intermediate point in the path of the bore by the curved guide coupled to the other lever;

(b) said one of the cutting bits is then withdrawn relative to the housing back away from the intermediate point in the path of the bore; and then (c) the other of the cutting bits is moved relative to the housing past the intermediate point to complete the bore, thereby avoiding interference between the pair of cutting bits.

3. The apparatus of claim 2, further comprising a control for actuating the prime mover, said trigger activating the control as the trigger is pivotally moved from a rest position, thereby initiating application of the driving force to the cutting bits as they are advanced to produce the curved bore.

4. The apparatus of claim 1, further comprising a trigger, the controlling means including a linkage mechanically coupling the trigger to both levers, said linkage coupling the trigger to the levers so that movement of the trigger in only one direction causes one of the levers to pivotally move relative to the housing in a first direction and then in a second direction that is opposite the first direction, and the other lever to move relative to the housing only in a first direction, said one of the levers thereby initially advancing one of the cutting bits to pivot relative to the housing past an intermediate point in the path of the curved bore and then retracting said one of the cutting bits relative to the housing as the other of the cutting bits advances relative to the housing past the intermediate point from the opposite end of the path to complete the curved bore.

5. The apparatus of claim 4, wherein said linkage comprises a pair of cams rotatably driven by movement of said trigger and having a surface of rotation, each of the pair of levers following the surface of rotation of a different one of the pair of cams, each cam having a shape determining the movement of the lever tracking along its surface of rotation so that said movement is different from that of the other lever.

6. The apparatus of claim 4, wherein said linkage comprises a ramp surface on the trigger, each of the levers contacting and tracking along a different portion of the ramped surface so that movement of the trigger causes the levers to move differently.

7. The apparatus of claim 4, further comprising means for adjusting an extent by which pivotal movement of the levers moves the curved guides and the cutting bits, so as to produce curved bores of different radii using curved guides of correspondingly different radii.

8. The apparatus of claim 7, wherein the means for adjusting comprise a pair of links, each link extending between one of the curved guides and one of the levers and having an angled portion adjacent to said one of the levers that is formed at an angle selected to contact said one lever at a defined distance from its pivot pin, said distance determining a range of pivotal motion of a selected curved guide having a specific radius of curvature.

9. The apparatus of claim 1, wherein said housing comprises a handle portion, and a removable cartridge portion through which said flexible cables extend, said pair of curved guides being disposed and pivotally mounted in the removable cartridge portion; further comprising disconnectable drive couplings that mechanically couple the prime mover to the flexible cables, and disconnectable links that mechanically couple the levers to the curved guides, so that the removable cartridge and flexible cables can readily be attached and disconnected from the handle portion and disconnectable drive couplings, respectively.

10. The apparatus of claim 9, wherein the cartridge portion is sized to engage the handle portion, and the disconnectable links each comprise two sections that releasably couple together; further comprising means for unlatching the two sections of each of the disconnectable links when the cartridge portion is removed from the handle portion.

11. The apparatus of claim 10, wherein the disconnectable links each comprise a spring biased pin on one section of the disconnectable link that engages an orifice on the other section of the disconnectable link; and wherein the means for unlatching comprise a release pin on the handle portion that acts on the spring biased pin to open the latch for removing the cartridge portion from the handle portion.

12. A method for drilling curved bores in an object comprising the steps of:

(a) providing a rotational drive force along two spaced-apart, substantially parallel axes;

(b) coupling a pair of flexible cables to the rotational drive force so that each flexible cable rotates about one of said axes, each flexible cable having a proximal end to which the rotational drive force is coupled and a distal end coupled to a cutting bit;

(c) positioning the cutting bits adjacent to the object and supporting the distal ends of the flexible cables and the cutting bits in curved guides;

(d) rotating the curved guides to move the cutting bits in coplanar arcs that intersect; and (e) pivotally rotating a pair of levers connected to the curved guides to advance the curved guides through an intersecting portion of their coplanar arcs at different times, to produce the curved bore in the object without the cutting bits contacting each other.

13. The method of claim 12, wherein one of the levers comprises a trigger that applies force to pivotally rotate the other lever, and wherein the step of pivotally rotating the pair of levers comprises the steps of pivotally rotating the other lever in first one direction and then in an opposite direction as the trigger is pivoted in only one direction, so that:

(a) one of the cutting bits is carried past an intermediate point of the intersecting portion by the curved guide coupled to the other lever; and then (b) said one of the cutting bits is withdrawn back from the intermediate point; and then (c) the other of the cutting bits is carried past the intermediate point to complete the bore, without interfering with said one of the cutting bits.

14. The method of claim 12, further comprising the step of actuating the drive force that rotates the flexible cables by moving the trigger from a rest position, thereby applying the driving force to the cutting bits at about the same time that they begin to advance to produce the curved bore.

15. The method of claim 12, further comprising the step of:
   (a) coupling a trigger to the levers so that movement of the trigger in only one direction causes one of the levers to pivotally move in a first direction and then in a second and opposite direction, and the other lever to move only in a first direction; and thereby
   (b) initially advancing one of the cutting bits to pivot past an intermediate point in the intersecting portion and then retracting said one of the cutting bits as the other of the cutting bits advances past the intermediate point from the opposite end of the path, to complete the curved bore.

16. The method of claim 12, further comprising the step of adjusting an extent by which pivotal movement of the levers moves the curved guides and the cutting bits, to produce curved bores of different radii using curved guides of corresponding radii.

17. The method of claim 16, wherein the step of adjusting comprises the step of providing a pair of links, each link extending between one of the curved guides and one of the levers, said links having an angled portion adjacent the levers that is formed at an angle; and selecting the angle so that each link contacts one of the levers at a defined distance from a pivot pin of the lever, said distance determining a range of pivotal motion for a selected curved guide having a specific radius of curvature.

18. The method of claim 12, wherein said pair of curved guides are pivotally mounted in a removable cartridge, further comprising the steps of disconnectably mechanically coupling the drive force to the flexible cables and disconnectably linking the levers to the curved guides, so that the removable cartridge and flexible cables can readily be replaced.

19. The method of claim 18, wherein the removable cartridge is sized to engage a handle, further comprising the step of releasably latching together sections of disconnectable links that couple the drive force to the flexible cables, when the cartridge is engaged with the handle.

20. The method of claim 19, further comprising the step of providing a finger release to unlatch the cartridge from the handle.

21. Apparatus for drilling a bore, comprising:
   (a) a prime mover for providing drilling energy;
   (b) a pair of drive transfer members, each drive transfer member having a proximal end operably coupled to the prime mover and a distal end operably coupled to a cutting member, for transfer of cutting energy from the prime mover to the cutting member;
   (c) a housing through which the drive transfer members extend, said housing having a distal end;
   (d) a pair of guides mounted for movement relative to the housing along respective paths that intersect at a location fixed relative to the housing, each guide supporting the distal end of one of the drive transfer members, so that as said pair of guides are moved toward each other from the distal end of the housing, they define a continuous composite path defined by the cutting members as they are moved relative to the housing, said cutting members being supported by the guides; and
   (e) means for controlling the movement of the guides so as to advance the cutting members relative to the housing along a common portion of the path at different times, to produce the bore without the cutting members contacting each other.

22. The apparatus of claim 21, wherein the controlling means includes a trigger and means coupled to the trigger for moving one of the guides relative to the housing in a first direction and then in an opposite direction as the trigger is moved in only one direction, so that:
   (a) one of the cutting members is moved relative to the housing past an intermediate point in the path;
   (b) said one of the cutting members is then withdrawn relative to the housing back away from the intermediate point; and then
   (c) the other of the cutting members is moved relative to the housing past the intermediate point to complete the bore, thereby avoiding interference between the pair of cutting members.

23. The apparatus of claim 21, in which the guides are curved and are pivotally mounted to swing relative to the housing in coplanar arcs that intersect.

24. The apparatus of claim 23, wherein the controlling means includes a trigger and means coupled to the trigger for swinging one of the curved guides relative to the housing in first one direction and then in an opposite direction as the trigger is pivoted in only one direction, so that:
   (a) one of the cutting members is moved relative to the housing past an intermediate point in the path;
   (b) said one of the cutting bits is then withdrawn relative to the housing back away from the intermediate point in the path of the bore; and then
   (c) the other of the cutting members is moved relative to the housing past the intermediate point to complete the bore, thereby avoiding interference between the pair of cutting members.

25. The apparatus of claim 23, wherein the housing comprises a handle portion and a removable cartridge portion through which the drive transfer members extend, the pair of guides being disposed and movably mounted in the removable cartridge portion; further comprising disconnectable drive couplings that mechanically couple the prime mover to the drive transfer members, and disconnectable links mechanically coupled to the curved guides, so that the removable cartridge and drive transfer members can readily be attached and disconnected from the handle portion and disconnectable drive couplings, respectively.

26. A method for drilling a bore in an object comprising the steps of:
   (a) providing rotational drive threes to two separate cutting members, each of such cutting members being mounted in a common housing for movement relatively toward and away from each other; and
   (b) moving the cutting members along respective curved paths through the object which paths intersect, in coordinated timed fashion such that one of the cutting members moves first to and then away from a point of intersection of the paths, followed by movement of the other cutting member to the point of intersection to complete the bore, without the cutting bits interfering with each other.

27. A method for drilling a bore in an object comprising the steps of:
   (a) providing rotational drive forces to two separate cutting members, each of such cutting members being mounted in a common housing for movement relatively toward and away from each other;
   (b) moving the cutting members along respective paths through the object which paths intersect, in coordinated timed fashion such that one of the cutting members moves first to and then away from a point of intersection of the paths, followed by movement of the other cutting member to the point of intersection to complete the bore, without the cutting members interfering with each other; and including (c) controlling movement of the cutting members by moving a trigger in one direction relative to the housing, such trigger being interconnected with the cutting members such that during such movement of the trigger in such one direction, one of the cutting members is moved to and then away from the intersection point, followed by movement of the other of the cutting members to the intersection point to complete the bore.

28. The method of claim 27, in which at least one of the cutting members is moved along a curved path.

29. A method for drilling a bore in an object comprising the steps of:

(a) providing rotational drive forces to two separate cutting members, each of such cutting members being mounted in a common housing for movement relatively toward and away from each other;

(b) moving one of the cutting members along a curved path through the object; and (c) moving the other cutting member along a path through the object which intersects the curved path, the cutting members being moved along their respective paths in coordinated timed fashion such that one of the cutting members moves first to and then away from a point of intersection of the paths, followed by movement of the other cutting member to the point of intersection to complete the bore, without the cutting members interfering with each other.

* * * * *

UNITED STATES PATENT AND TRADEMARK OFFICE
CERTIFICATE OF CORRECTION

PATENT NO. : 5,509,918
DATED : April 23, 1996
INVENTOR(S) : J.W. Romano

It is certified that error appears in the above-indentified patent and that said Letters Patent is hereby corrected as shown below:

| COLUMN | LINE | |
|---|---|---|
| 18 (Claim 26, | 48 line 48) | "threes" should read --forces-- |

Signed and Sealed this

Third Day of December, 1996

Attest:

BRUCE LEHMAN

*Attesting Officer*     *Commissioner of Patents and Trademarks*